(12) United States Patent
Lopez

(10) Patent No.: US 10,997,721 B2
(45) Date of Patent: May 4, 2021

(54) MICROBE SCANNING DEVICE AND METHODS THEREOF

(71) Applicant: Beth Allison Lopez, Whittier, CA (US)

(72) Inventor: Beth Allison Lopez, Whittier, CA (US)

( * ) Notice: Subject to any disclaimer, the term of this patent is extended or adjusted under 35 U.S.C. 154(b) by 0 days.

(21) Appl. No.: 16/842,630

(22) Filed: Apr. 7, 2020

(65) Prior Publication Data
US 2020/0357114 A1 Nov. 12, 2020

Related U.S. Application Data

(60) Provisional application No. 62/843,876, filed on May 6, 2019, provisional application No. 62/911,007, filed on Oct. 4, 2019.

(51) Int. Cl.
*G06K 9/00* (2006.01)
*G06T 7/00* (2017.01)
*C12Q 1/04* (2006.01)

(52) U.S. Cl.
CPC .............. *G06T 7/0012* (2013.01); *C12Q 1/04* (2013.01); *G06T 2207/10008* (2013.01); *G06T 2207/10048* (2013.01); *G06T 2207/10056* (2013.01); *G06T 2207/30088* (2013.01)

(58) Field of Classification Search
CPC . G06T 2207/10048; G06T 2207/30088; G06T 2207/10056; G06T 2207/10008; G06T 7/0012; C12Q 1/04
See application file for complete search history.

(56) References Cited

U.S. PATENT DOCUMENTS

| | | | | |
|---|---|---|---|---|
| 9,922,412 | B1* | 3/2018 | Freeman | G06K 9/6215 |
| 10,660,482 | B2* | 5/2020 | Kamatchi | G05B 19/05 |
| 2013/0192451 | A1* | 8/2013 | Scott | F41G 3/147 |
| | | | | 89/41.05 |
| 2015/0058368 | A1* | 2/2015 | Hyde | G16H 20/13 |
| | | | | 707/756 |
| 2016/0358332 | A1* | 12/2016 | Watanabe | G06T 7/0012 |
| 2017/0316255 | A1* | 11/2017 | Arata | G06T 7/251 |
| 2018/0276439 | A1* | 9/2018 | Strohmann | G06K 9/0012 |
| 2018/0310890 | A1* | 11/2018 | Li | A61B 5/7275 |

* cited by examiner

*Primary Examiner* — Amara Abdi

(57) ABSTRACT

A microbe scanning device and methods are disclosed. The device includes a housing that includes a sensor(s), output device(s) that conveys text/audio/images, and control circuit(s) coupled to the sensor(s) and output device(s). the sensor captures first ASD and second ASD. The first and second ASD each includes an image of an appendage captured using one or more of radio waves, visible light ("VL"), and infrared light ("IR"). The control circuit is configured to determine, using ASD, whether a user is present; determine, using ASD, whether hands are present when the user is present; determine, using ASD, whether microbiol material is present on the hands; generate a notification when the microbial material is present on the hands; transmit, via the output device, the notification; generate a notification when the microbial material is not present on the hands; and transmit the second notification when generated.

18 Claims, 5 Drawing Sheets

MICROBE SCANNING DEVICE AND METHODS THEREOF

CROSS-REFERENCE TO RELATED APPLICATIONS

This application claims priority to U.S. Provisional Application No. 62/911,007 filed Oct. 4, 2019, which claims priority to U.S. Provisional Application No. 62/843,876 filed May 6, 2019, which are hereby incorporated herein by reference.

FIELD OF THE INVENTION

The present disclosure relates generally to scanning devices. More specifically, the present disclosure describes microbe scanning devices.

BACKGROUND OF THE INVENTION

Diseases such as the coronavirus disease 2019 ("Covid-19"), severe acute respiratory syndrome ("SARS"), bird flu (also called "avian influenza"), etc. have arguably resulted in an increase in societal public health concerns. To be sure, it is well-known that proper hand hygiene is essential to reduce the transmission of germs and bacteria from person to person. Public health issues can arise in areas where the public interacts frequently, which can potentially lead to an increase in the spread of germs and bacteria (e.g., medical facilities, food service industries, and other relevant or similarly related locations). Society often promotes proper hand hygiene using signages and other physical reminders in public (e.g., near a bathroom sink, door, entrance, and/or exit) to engage people on hand hygiene and public health issues.

Hand sanitizers (e.g., using wall-mounted units) are often utilized in public bathrooms for users; unfortunately, some individuals ignore societal norms of sanitizing their hands prior to exiting. Even more, current solutions to enforce hand sanitation can be incapable of regulating and monitoring individuals that are required to maintain proper hand hygiene.

BRIEF DESCRIPTION OF THE DRAWINGS

Some of the embodiments will be described in detail, with reference to the following figures, wherein like designations denote like members, wherein.

Figure 1:
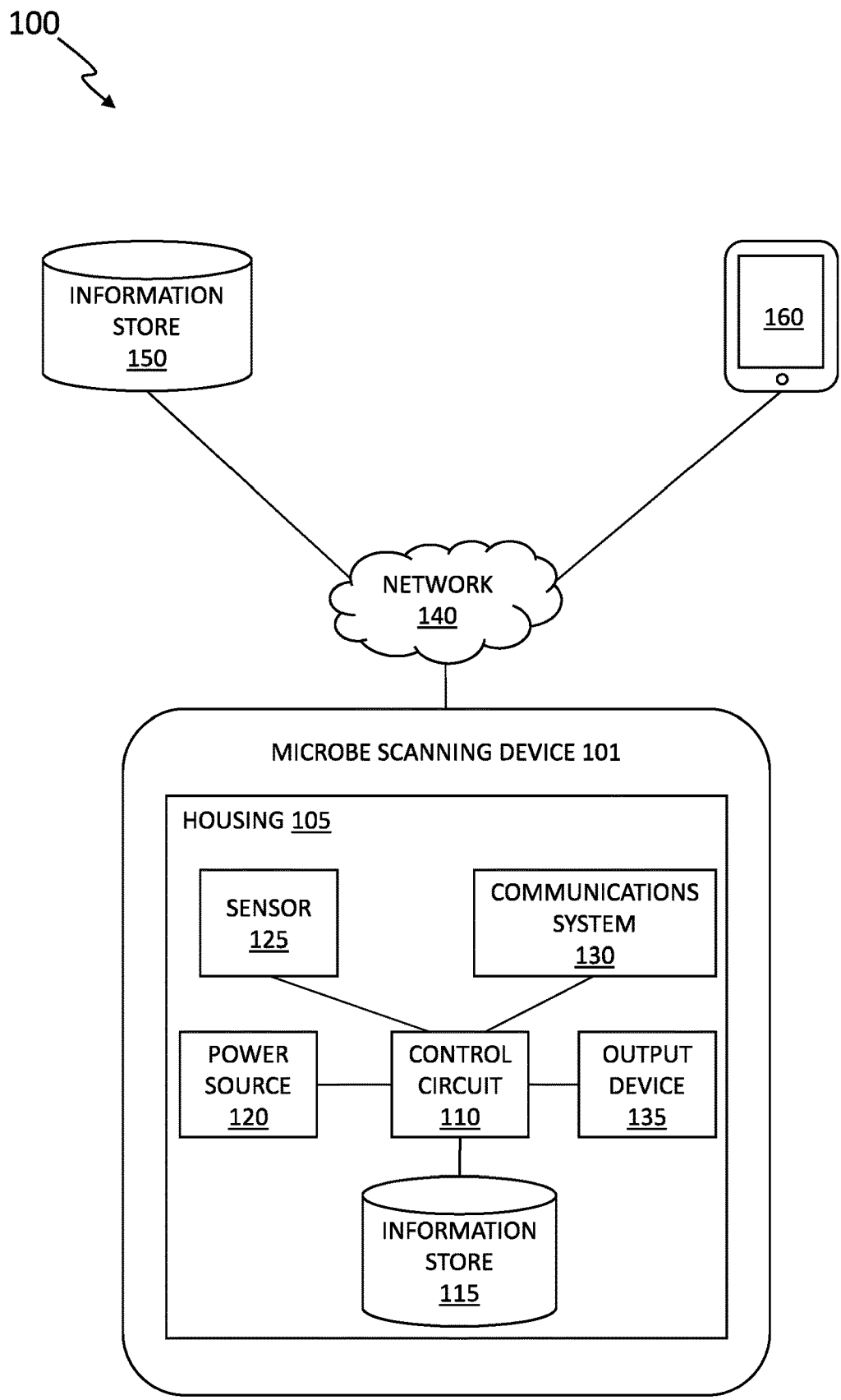
FIG. 1 is a block diagram that depicts a microbe scanning environment according to some embodiments.

Unless otherwise specifically noted, articles depicted in the drawings are not necessarily drawn to scale.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods.

Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification and are to be considered a portion of the entire written description of this invention.

The present disclosure includes many aspects and features. Moreover, while many aspects and features relate to, and are described in the context of microbial scanning devices and methods thereof, embodiments of the present disclosure are not limited to use only in this context.

Diseases such as the coronavirus disease 2019 ("Covid-19"), severe acute respiratory syndrome ("SARS"), bird flu (also called "avian influenza"), etc. have arguably resulted in an increase in societal public health concerns. To be sure, it is well-known that proper hand hygiene is essential to reduce the transmission of germs and bacteria from person to person. Public health issues can arise in areas where the public interacts frequently, which can potentially lead to an increase in the spread of germs and bacteria (e.g., medical facilities, food service industries, and other relevant or similarly related locations). Society often promotes proper hand hygiene using signages and other physical reminders in public (e.g., near a bathroom sink, door, entrance, and/or exit) to engage people on hand hygiene and public health issues.

Hand sanitizers (e.g., using wall-mounted units) are often utilized in public bathrooms for users; unfortunately, some individuals ignore societal norms of sanitizing their hands prior to exiting. Even more, current solutions to enforce hand sanitation can be incapable of regulating and monitoring individuals that are required to maintain proper hand hygiene.

FIG. 1. is a block diagram that depicts a microbe scanning environment, generally 100 according to some embodiments. The instant disclosure seeks to provide a microbe scanning device that scans user's hands for microbes, records scan data, generates notifications, and communicates wirelessly, in accordance with preferred embodiments. Environment 100 includes computing device 160, information store 150, and microbe scanning device ("MSD") 101 all interconnected via network 140. Network 140 can be a distributed computing environment, for example, an intranet (e.g., local area networks and wide area networks) and/or the Internet. The computing device 160 is one or more machines that can be instructed to carry out sequences of arithmetic or logical operations automatically via computer programming (e.g., desktop computers, laptop computers, thin clients, servers, cluster computers, smart TVs, in-vehicle computing devices, wearable computing devices, mobile computing devices, for example, smartphones, phablets, tablets, computing devices that can use cellular data communication protocols and/or wireless local area network protocols, or a combination of two or more thereof)). In general, the computing device 160 can be any device capable of communicating with the MSD 101 via the network 140.

The computing device 160 preferably receives notifications from the MSD 101. In some embodiments, the computing device 160 is associated with an access control system that, e.g., restricts access to a location and/or resources. In other embodiments, the computing device 160 is associated with an individual(s) and or systems required to monitor user hand hygiene (e.g., managers and supervisors). The information store 150 is an organized collection of data (e.g., hand scans, user biometric data, notification, user scan history, similar data generated by the MSD 101), generally stored and accessed electronically from a computer system. The information store 150 preferably stores user hand scans and/or notifications generated by the MSD 101. The information store 150 and the computing device 160 are a single unit or system, in accordance with other embodiments. The information store 150 can allow access to hand scans and/or notifications generated by the MSD 101.

The MSD 101 includes a housing 105 where one or more information stores 115, output devices 135, communications systems 130, power sources 120, sensors 125 or a combination of two or more thereof are communicatively coupled to one or more control circuits 110. The control circuit 110 includes one or more circuits configured to perform at least one of the steps, processes, methods, and/or functions described herein. The housing 105 can include any shape, size, material, features, type or kind, components, quantity of components, arrangements of components as well as be positioned in any location and/or orientation that would fulfill the objectives and intents of the instant disclosure. The housing 105 is preferably at least about the width of a human adult head and/or hand(s.) The housing 105 can include polymeric material to facilitate overall weight reduction and/or promote impact resistance (e.g., ABS, polycarbonate, PPSU, and UHMW). In preferred embodiments, the housing 105 is configured for surface (e.g., wall, counter tops, as well as similar stationary locations) mounting of the MSD 101. In other embodiments, the MSD 101 is a handheld device (i.e. a device small enough to hold and operate in the hand). In handheld embodiments, for example, the housing 105 has an overall size and/or shape that is small enough to hold and operate in the hand.

The information store 115 functions in a similar manner to the information store 150. The information store 115 is an organized collection of data (e.g., hand scans, user biometric data, notification, user scan history, first notifications, second notifications, similar data generated by the MSD 101), generally stored and accessed electronically from a computer system. The information store 115 preferably stores user hand scans and/or notifications generated by the MSD 101. The information store 115 can include one or more databases performing tasks interoperably. The output device 135 is one or more computer hardware devices that convert information into human-comprehensible form (e.g., text, images, tactile, audio, and video). The output device 135 preferably includes a speaker(s). In some embodiments, the output device 135 includes a computer monitor (e.g., touchscreen monitors). In general, the output device 135 may be any piece of computer hardware equipment that converts information into human-readable form, in accordance with some embodiments.

The communications system 130 is preferably a two-way radio transceiver. The communications system 130 can be a plurality of devices working together. The communications system 130 is preferably configured to communicate via the network 140 using one or more wireless communications protocols (e.g., LTE, Wi-Fi, Bluetooth, 4G, 5G, etc.) The power source 120 is an electrical device that supplies electric power to the MSD 101 according to preferred embodiments. For example, the power supply 120 can couple to an electrical outlet to draw power therefrom. In other embodiments, the power source 120 includes one or more primary batteries (i.e. disposable batteries) and/or secondary batteries (i.e. rechargeable batteries).

The sensor 125 is preferably one or more devices, modules, machines, or subsystems that detect events or changes in the ambient environment or the MSD 101 and send the information to the control circuit 110. In general, the sensor 125 can be any type, kind, shape and/or size; include any features, components, quantity of components, arrangements of components; as well as be positioned in any location and/or orientation that would fulfill the objectives and intents of the instant disclosure. The sensor 125 captures data (e.g., images and scans) using radio waves ("RF"), visible light ("VL"), and/or infrared light ("IR"). The sensor 125 captures first appendage sensor data ("ASD") and second ASD, which each include one or more images of an appendage captured using radio waves ("RF"), VL, and/or IR. As used herein, the term "appendage" preferably refers to a human head and/or hands.

Figure 2:
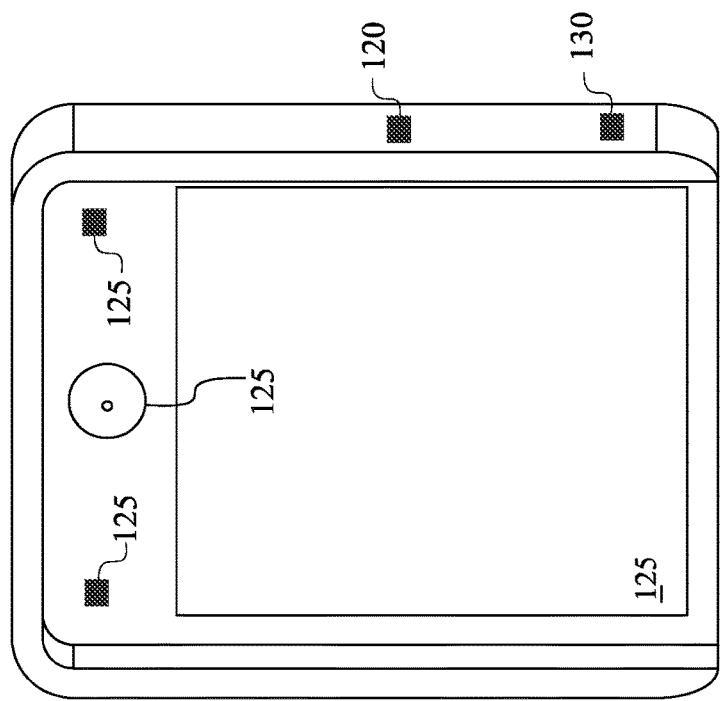
FIG. 2 illustrates a user positioned proximate to a microbe scanning device according to other embodiments.
Figure 2:
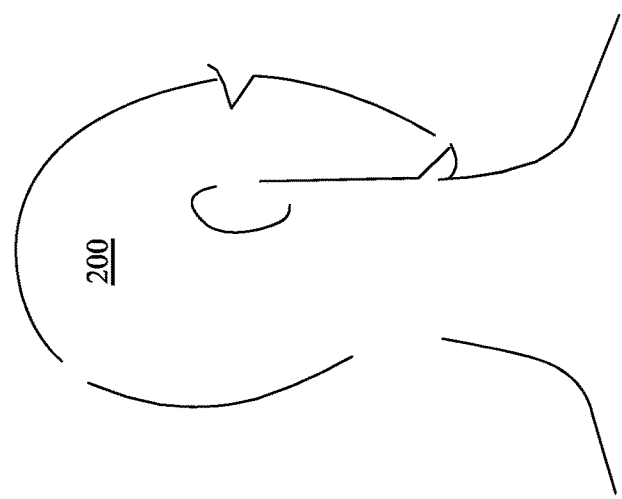

FIG. 2 illustrates a user positioned proximate to the MSD 101 according to other embodiments. In an alternative embodiment of the present invention, the MSD 101 can be a handheld wand or similar object. This alternative embodiment would allow for the user to utilize the MSD 101 to scan over a given surface area for microbial material and such. In some embodiments, the housing 105 can include an automated cleaning mechanism in which the automated cleaning mechanism can sanitize the surface of the 105 when a user accidentally places their palm(s) on the MSD 101 (e.g., which can result in false positive readings of scans of the user's hand(s).

According to yet still other embodiments, the MSD 101 can include processes and/or steps that can prevent access to entryways, exits, particular equipment or tools, and/or other relevant objects that must remain as sterile as possible or can be easily contaminate by the touch of a user's hand(s) that may not be properly sanitized. In an alternative embodiment, the MSD 101 can be linked to the door, or similar objects, to open the door if the user passes the hygiene check of the present invention, this would prevent a person from having to touch potentially dirty door handles, such as when exiting a bathroom. Alternatively, if the scanning does not pass, the auto door opening can be bypassed, however it will be recorded, and management would be notified.

Figure 3:
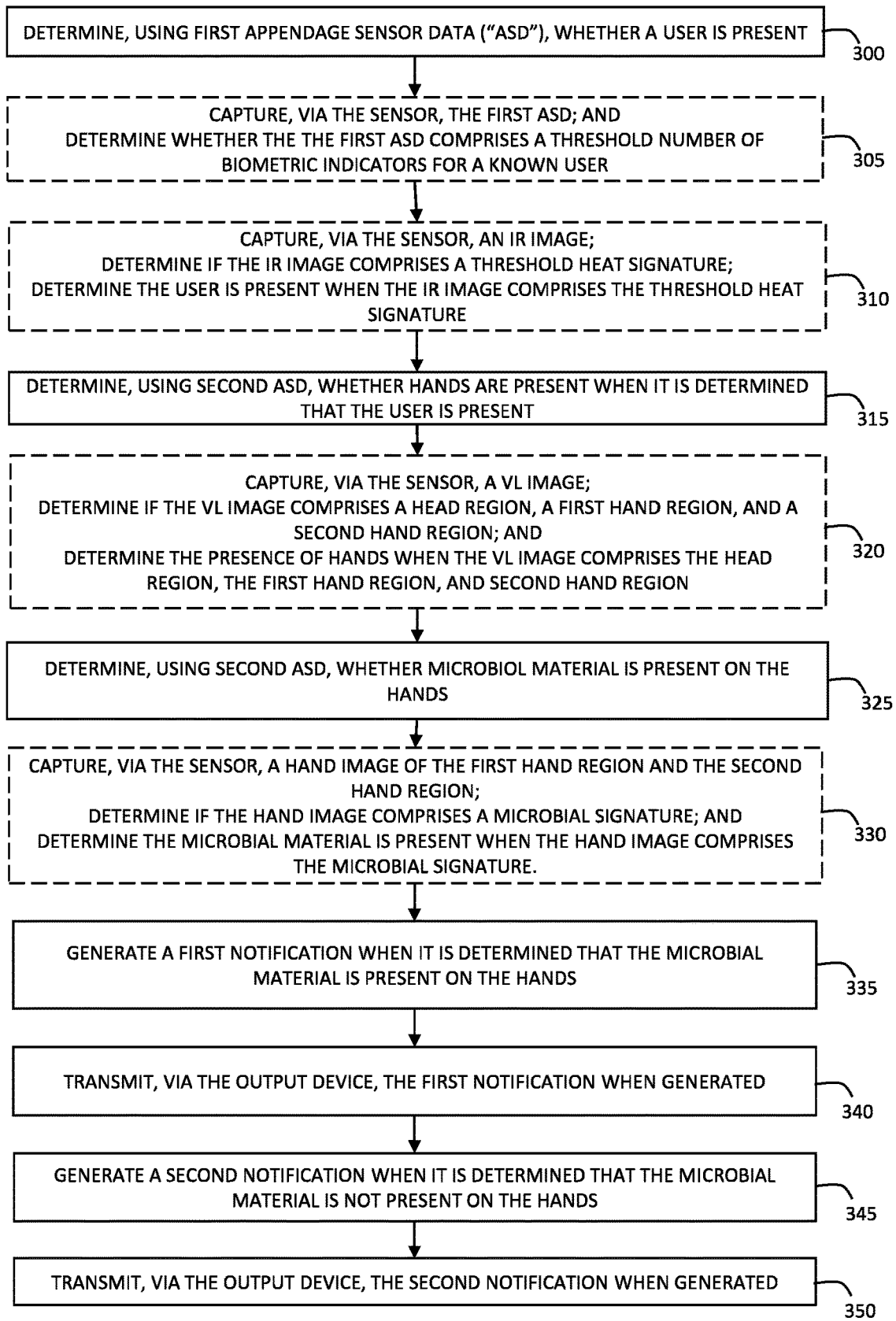
FIG. 3 illustrates the processing steps for scanning microbial material via the microbe scanning device according to some embodiments.

The method of FIG. 3 preferably initiates when the user approaches the MSD 101. At step 300, whether a user (e.g., user 200) is present is determined user first ASD. For example, first ASD can include identifying information associated with various users (e.g., the user 200). Although the first ASD can include various forms and/or types of identifying information, the first ASD preferably includes one or more biometric indicators (e.g., fingerprint, palm veins, face recognition, DNA, palm print, hand geometry, iris recognition, retina and odor/scent. For example, at step 305, the first ASD is captured via the sensor 125 and whether the first ASD includes a threshold number of biometric indicators for a known user is determined. Here, the biometric indicator use allows users to be identified with a high probability of certainty, which is useful in controlling access to high risk resources and/or environments. Applicable biometric indicators include, but are not limited to, fingerprints, a palm vein, a facial feature, a palm print, a hand geometry, an iris pattern, a retinal pattern In embodiments where identity verification is not specifically warranted, determinations of the user's presence is sufficient. For example, at Step 310, an IR image is captured by the sensor 125; whether the IR image includes a threshold heat signature (e.g., of a human appendage) is determined; and the user is determined to be present when the IR image includes the threshold heat signature. For example, threshold heat signatures can be determined using the average heat signature of a statistically significant number of human appendages. At step 315, whether hands are present is determined when it is determined that the user is present. For example, the user is prompted to display their hands to the MSD 101 for recording. At step 320, one or more VL images area captured using the sensor 125; whether the VL image(s) (e.g., VL image 400) includes a head region 420, a first hand region 410, and a second hand region 415 is determined; and the presence of the hands is determined when the VL image(s) comprises the head region, the first hand region, and the second hand region.

Figure 4:
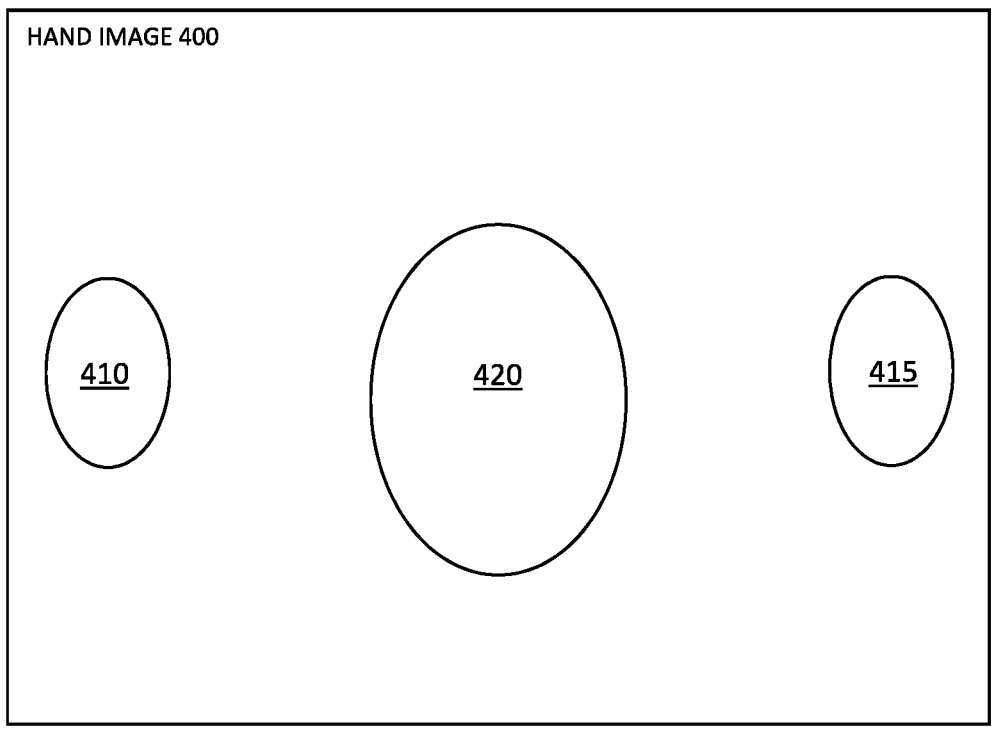
FIG. 4 depicts a VL image that includes a first hand region, second hand region, and head region, in accordance with preferred embodiments.

FIG. 4 depicts a VL image 400 that includes the first hand region 410, the second hand region 415, and the head region 420, in accordance with preferred embodiments. For example, the user 200 presents themselves to the sensor 125 holding their hands palms out and level with their head. The sensor 125 captures the VL image, which is analyzed for the presence of a substantially oval structure (i.e. the head region 420) positioned between two smaller substantially oval structures (i.e. the first hand region 410 and the second hand region 415). In other words, the VL image 400 includes the first hand region 410 positioned proximate to the head region 420 and the second hand region 415 positioned proximate to the head region 420 opposite the first hand region 410.

In some embodiments, the output device 135 includes a display screen that displays instructions, notifications, a user interface, and/or user biometric indicators.

Subsequent to identifying the user and/or determining their presence the presence of microbial material can be determined. At Step 325, whether microbial material is present of the hands is determined. For example, at Step 330, one or more hand images of the first hand region and the second hand region are captured using the sensor 125; whether the hand image includes a microbial signature(s); and determine that the microbial material is present when the hand image includes the microbial signature. For example, the hand image is preferably captured using radio waves, IR, VL, or a combination of two or more thereof. The MSD 101 notifies the user 200 of the scan results. In preferred embodiments, the MSD 101 generates first notifications and second notifications that each include audio, text, visual indicator(s), and/or image(s). In some embodiments, first and/or second notification are stored in the information store 115. The first notification preferably conveys that the microbial material is present on the hands of the user and require removal via cleaning.

The second notification conveys that the microbial material is not present on the user hands. At Step 335, a first notification is generated when it is determined that the microbial material is present on the hands of the user. At Step 340, the first notification is transmitted, e.g., via the output device 135, when the first notification is generated. For example, the first notification can be an audio and/or text message that instructs the user to cleanse their hand again. In other embodiments, the first notification can include visual indicators (e.g., a red light(s), terms/phrases that indicate "stop" and/or "fail", or similar visual indicators) that instruct the user to cleanse their hands again.

The first notification and second notifications are transmitted via the output device 135 to notify the user 200. In certain embodiments, the first notification and second notifications are transmitted via the output device 135 to notify the user 200 and those within the ambient environment relative to the MSD 101. At step 345, the second notification is generated when it is determined that the microbial material is not present on the hands of the user. At step 350, the second notification is transmitted, e.g., via the output device 135, when generated. In some embodiments, first notifications and/or second notifications are transmitted via the communication system 130. In certain embodiments, first notifications and/or second notifications are transmitted to computing device 160. In other embodiments, first notifications and second notifications are transmitted to the information store 150.

Figure 5:
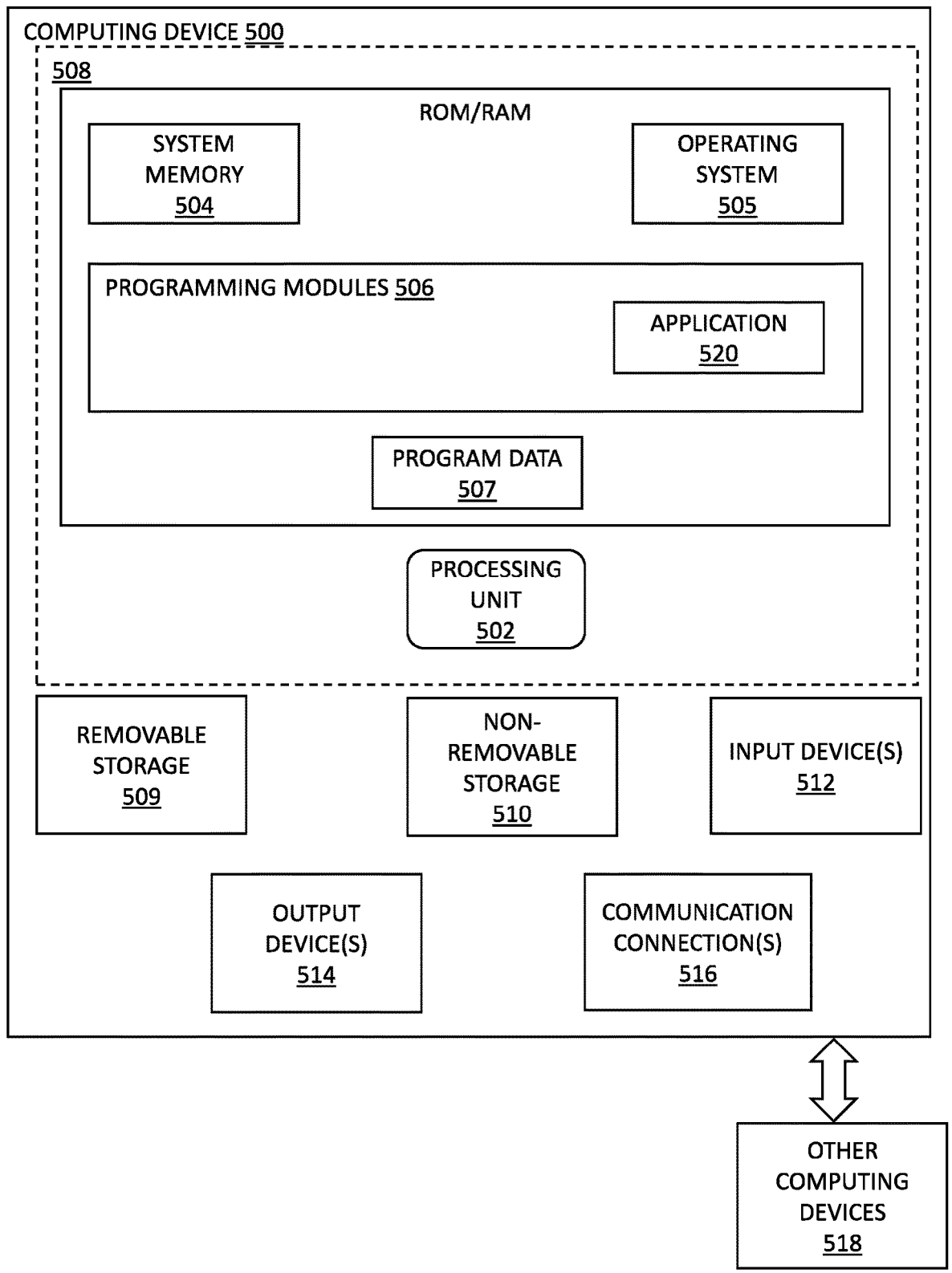
FIG. 5 illustrates an exemplary system for implementing at least some of the disclosed processes, in accordance with certain embodiments.

With reference to FIG. 5, a system consistent with an embodiment of the disclosure may include a computing device or cloud service, such as computing device 500. Computing device 500 can represent the computing device 160 and the MSD 101. In a basic configuration, computing device 500 may include at least one processing unit 502 (e.g., control circuit 110) and a system memory 504. Depending on the configuration and type of computing device, system memory 504 may comprise, but is not limited to, volatile (e.g. random-access memory (RAM)), non-volatile (e.g. read-only memory (ROM)), flash memory, or any combination. System memory 504 may include operating system 505, one or more programming modules 506, and may include a program data 507. Operating system 505, for example, may be suitable for controlling computing device 500's operation. In one embodiment, programming modules 506 may include machine learning module. Furthermore, embodiments of the disclosure may be practiced in conjunction with a graphics library, other operating systems, or any other application program and is not limited to any particular application or system. This basic configuration is illustrated in FIG. 5 by those components within a dashed line 508.

Computing device 500 may have additional features or functionality. For example, computing device 500 may also include additional data storage devices (removable and/or non-removable) such as, for example, magnetic disks, optical disks, or tape. Such additional storage is illustrated in FIG. 5 by a removable storage 509 and a non-removable storage 510. Computer storage media may include volatile and nonvolatile, removable and non-removable media implemented in any method or technology for storage of information, such as computer-readable instructions, data structures, program modules, or other data. System memory 504, removable storage 509, and non-removable storage 510 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 500. Any such computer storage media may be part of device 500. Computing device 500 may also have input device(s) 512 such as a keyboard, a mouse, a pen, a sound input device, a touch input device, a location sensor, a camera, a biometric sensor, etc. Output device(s) 514 such as a display, speakers, a printer, etc. may also be included. The aforementioned devices are examples and others may be used.

Computing device 500 may also contain a communication connection 516 that may allow device 500 to communicate with other computing devices 518, such as over a network in a distributed computing environment, for example, an intranet or the Internet. Communication connection 516 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 504, including operating system 505. While executing on processing unit 502 (e.g., control circuit 110), programming modules 506 (e.g., application 520 such as a media player) may perform processes including, for example, one or more stages of methods, algorithms, systems, applications, servers, databases as described above. The aforementioned process is an example, and processing unit 502 (e.g., control circuit 110) may perform other processes. Other programming modules that may be used in accordance with embodiments of the present disclosure may include machine learning application.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the disclosure has been explained in relation to its preferred embodiment, it is to be understood that many other possible modifications and variations can be made without departing from the spirit and scope of the disclosure.

The invention claimed is:

1. A microbe scanning device, comprising:
a housing comprising:
a sensor;
an output device configured to convey one or more of text, audio, and images;
a control circuit communicatively coupled to the sensor and the output device;
wherein
the sensor captures first appendage sensor data ("ASD") and second ASD;
the first ASD and second ASD each comprising an image of an appendage captured using one or more of radio waves, visible light ("VL"), and infrared light ("IR");
the control circuit is configured to:
determine, using first appendage sensor data ("ASD"), whether a user is present;
determine, using second ASD, whether hands are present when it is determined that the user is present;
determine, using second ASD, whether microbial material is present on the hands;
generate a first notification when it is determined that the microbial material is present on the hands;
transmit, via the output device, the first notification when generated;
generate a second notification when it is determined that the microbial material is not present on the hands; and
transmit, via the output device, the second notification when generated;
wherein
the first ASD comprises biometric indicators;
in determining whether the user is present the control circuit is configured to:
capture, via the sensor, the first ASD; and
determine whether the first ASD comprises a threshold number of biometric indicators for a known user;
wherein in determining whether hands are present the control circuit is configured to:
capture, via the sensor, a VL image;
determine if the VL image comprises:
a head region,
a first hand region positioned proximate to the head region,
a second hand region positioned proximate to the head region opposite the first hand region;
the head region being level with the first hand region and the second hand region; and
determine the presence of hands when the VL image comprises the head region, the first hand region, and second hand region.

2. The device of claim 1, wherein the biometric indicator comprises a fingerprint, a palm vein, a facial feature, a palm print, a hand geometry, an iris pattern, a retinal pattern.

3. The device of claim 1, wherein the output device comprises one or more of a visual display unit, a speaker, and a touch screen.

4. The device of claim 3, wherein in determining whether the user is present the control circuit is configured to:
capture, via the sensor, an IR image;
determine if the IR image comprises a threshold heat signature; AND determine the user is present when the IR image comprises the threshold heat signature.

5. The device of claim 1, wherein in determining whether the microbial material is present the control circuit is configured to:
capture, via the sensor, a hand image of the first hand region and the second hand region using one or more of radio waves, IR, and VL;
determine if the hand image comprises a microbial signature; and
determine the microbial material is present when the hand image comprises the microbial signature.

6. The device of claim 5, wherein the first notification comprises one or more of audio, text, a visual indicator, and an images; and
conveys that the microbial material is present on the hands and requires removal via cleaning.

7. The device of claim 6, wherein the second notification comprises one or more of audio, text, a visual indicator, and an images; and
conveys that the microbial material is not present on the user hands.

8. The device of claim 7, further comprising:
a communications device;
wherein
the control circuit is communicatively coupled to the communications device; and
the control circuit is configured to transmit, via the communications device, one or more of the first notification and the second notification.

9. A method to enable microbe scanning, comprising:
determining, via a control circuit, whether a user is present using first appendage sensor data ("ASD"), the first ASD captured via a sensor, the sensor configured to capture first ASD and second ASD, the first ASD and the second ASD each comprising an image of an appendage captured using one or more of visible light ("VL") and infrared light ("IR");
determining, via the control circuit, whether hands are present using second ASD when it is determined that the user is present, the second ASD captured via the sensor;
determining, via the control circuit, whether microbial material is present on the hands using the second ASD;
generating, via the control circuit, a first notification when it is determined that the microbial material is present on the hands;
transmitting, via the control circuit, the first notification using an output device;
generating, via the control circuit, a second notification when it is determined that the microbial material is not present on the hands; and
transmitting, via the control circuit, the second notification using the output device;
wherein determining whether the user is present comprises:
capturing, via the control circuit, the first ASD using the sensor; and
determining whether the first ASD the first ASD comprises a threshold number of biometric indicators for a known user;
wherein determining whether the hands are present comprises:
capturing, via the control circuit, a VL image using the sensor;
determining, via the control circuit, if the VL image comprises:
a head region;
a first hand region positioned proximate to the head region; and
a second hand region positioned proximate to the head region opposite the first hand region;
the head region being level with the first hand region and the second hand region; and
determining, via the control circuit, the hands are present when the VL image comprises the head region, the first hand region, and second hand region.

10. The method of claim 9, wherein the biometric indicator comprises a fingerprint, a palm vein, a facial feature, a palm print, a hand geometry, an iris pattern, a retinal pattern.

11. The method of claim 9, wherein the output device comprises one or more of a visual display unit, a speaker, and a touch screen.

12. The method of claim 11, wherein determining, via the control circuit, whether the user is present comprises:
capturing, via the control circuit, an IR image using the sensor;
determining, via the control circuit, if the IR image comprises a threshold heat signature;
determining, via the control circuit, the user is present when the IR image comprises the threshold heat signature.

13. The method of claim 1, wherein determining whether the microbial material is present comprises:
capturing, via the control circuit, a hand image of the first hand region and the second hand region using the sensor, the sensor capturing the hand image using one or more of radio waves, IR, and VL;
determining, via the control circuit, if the hand image comprises a microbial signature; and
determining, via the control circuit, the microbial material is present when the hand image comprises the microbial signature.

14. The method of claim 13, wherein the first notification comprises one or more of audio, text, a visual indicator, and an images; and
conveys that the microbial material is present on the hands and requires removal via cleaning.

15. The method of claim 14, wherein the second notification comprises one or more of audio, text, a visual indicator, and an images; and
conveys that the microbial material is not present on the hands.

16. The method of claim 15, further comprising transmitting, via the control circuit, one or more of the first notification and the second notification using a communications device.

17. The device of claim 1, wherein the biometric indicator comprises DNA and odor/scent.

18. The method of claim 9, wherein the biometric indicator comprises DNA and odor/scent.

* * * * *